US011135373B2

(12) United States Patent
Bilgic (10) Patent No.: US 11,135,373 B2
(45) Date of Patent: Oct. 5, 2021

(54) DRUG DELIVERY DEVICE FOR LIQUID PHARMACEUTICALS

(71) Applicant: Sima Patent ve Lisanslama Hizmetleri Ltd. Sti., Istanbul (TR)

(72) Inventor: Mahmut Bilgic, Istanbul (TR)

(73) Assignee: Sima Patent ve Lisanslama Hizmetleri Ltd. Sti., Esenler/Istanbul (TR)

( * ) Notice: Subject to any disclaimer, the term of this patent is extended or adjusted under 35 U.S.C. 154(b) by 77 days.

(21) Appl. No.: 16/098,060

(22) PCT Filed: Feb. 17, 2017

(86) PCT No.: PCT/EP2017/053574
§ 371 (c)(1),
(2) Date: Oct. 31, 2018

(87) PCT Pub. No.: WO2017/144352
PCT Pub. Date: Aug. 31, 2017

(65) Prior Publication Data
US 2019/0143049 A1    May 16, 2019

(30) Foreign Application Priority Data
Feb. 24, 2016    (EP) ..................................... 16000443

(51) Int. Cl.
*A61M 5/315* (2006.01)
*A61M 5/31* (2006.01)
(52) U.S. Cl.
CPC .... *A61M 5/31551* (2013.01); *A61M 5/31575* (2013.01); *A61M 5/31585* (2013.01);
(Continued)
(58) Field of Classification Search
CPC .......... A61M 5/31551; A61M 5/31585; A61M 5/31575; A61M 5/31541; A61M 5/31528; A61M 5/31558; A61M 5/3158
See application file for complete search history.

(56) References Cited

U.S. PATENT DOCUMENTS

2007/0244436 A1*  10/2007  Saiki ................. A61M 5/31551
                                                              604/131

FOREIGN PATENT DOCUMENTS

WO    WO-2006/037434 A1    4/2006

OTHER PUBLICATIONS

International Search Report and Written Opinion for International Application No. PCT/EP2017/053574, dated May 12, 2017 (10 pages).

(Continued)

*Primary Examiner* — Emily L Schmidt
(74) *Attorney, Agent, or Firm* — Clark & Elbing LLP (57) ABSTRACT

The present invention proposes a liquid pharmaceuticals delivery device (18) comprising a mainly cylindrical main body (1), a cartridge (3) having a mainly cylindrical inner cavity with a volumetric capacity for accommodating multiple doses of a liquid pharmaceutical, the cartridge (3) comprising a first end for receiving a plunger (7) and a second end for liquid pharmaceutical extraction. The device (18) further comprises a jackscrew (55) a comprising a threaded lower jackscrew (5) and a threaded upper jackscrew (6) integrated or fixed to each other. The jackscrew (55) being rotatable around a primary axis of the main body (1) and stationary along said primary axis, a threaded plunger rod (8) which is integrated to the plunger (7) and which has a thread diameter (Dp) corresponding to thread diameter of the lower jackscrew (5). A button (12) is engageable with the spindle (10), by one thereof having a recess and the other having a protrusion matching said recess along a direction parallel to the primary axis of the spindle (10). The threaded mainly cylindrical spindle (10) has a thread diameter (Ds) corresponding to thread diameter of the upper jackscrew (6). The thread diameter (Ds) of the (Continued)

spindle (10) is greater than the thread diameter (Dp) of the plunger rod (8).

10 Claims, 6 Drawing Sheets

(52) U.S. Cl.
CPC . *A61M 5/31541* (2013.01); *A61M 2005/3126* (2013.01); *A61M 2205/581* (2013.01); *A61M 2205/582* (2013.01)

(56) References Cited

OTHER PUBLICATIONS

International Preliminary Report on Patentability for International Application No. PCT/EP2017/053574, dated May 3, 2018 (28 pages).

\* cited by examiner

DRUG DELIVERY DEVICE FOR LIQUID PHARMACEUTICALS

TECHNICAL FIELD OF THE INVENTION

The present invention relates to a drug delivery device for subcutaneous administration of liquid pharmaceuticals.

BACKGROUND OF THE INVENTION

Pen-type injectors are widely used by patients applying regular injection without necessitation of formal medical training. Commonly, diabetic patients use such devices for effectively managing their personal treatment.

Pen-type injectors on the market usually have multiple snap-on connections in attaching a multi-dose cartridge and a driving mechanism, jeopardizing dose accuracy by mechanical instabilities due to tolerances and loose connections between interrelated parts. This causes variations in intended volumetric dosages and unpredictable force transmission errors.

High number of snap-on connections increases the risk of unintended disassembly of the device during or after injection. Furthermore, force required to be exerted onto the device is usually high, which causes inconvenience for those who are physically handicapped or elderly.

Assembly of the individual parts and final assembly of multi-dose cartridge onto the mechanical driving mechanism in such devices are also complicated and not sufficiently reliable.

Therefore, novel driving mechanisms and assembly manners are sought in pen-type injectors.

OBJECTS OF THE INVENTION

Primary object of the present invention is to overcome the above mentioned shortcomings of the prior art.

Another object of the present invention is obtainment of an easy-to-assemble, and easy-to-use drug delivery device with high mechanical stability.

A further object of the present invention is to provide a drug delivery device which is easy to use and requires relatively less force during subcutaneous self-administration.

SUMMARY OF THE INVENTION

The present invention proposes a liquid pharmaceuticals delivery device (18) comprising a mainly cylindrical main body (1), a cartridge (3) having a mainly cylindrical inner cavity with a volumetric capacity for accommodating multiple doses of a liquid pharmaceutical, the cartridge comprising a first end for receiving a plunger (7) and a second end for liquid pharmaceutical extraction; the plunger (7) having a circumferential portion shaped and sized to correspond to the transversal section of the cartridge (3), the device (18) further comprising a jackscrew (55) comprising a threaded lower jackscrew (5) and a threaded upper jackscrew (6) integrated or fixed to each other, the jackscrew (55) being rotatable around a primary axis (16) of the main body (1) and stationary along said primary axis (16), a threaded plunger rod (8) which is integrated to the plunger (7) and which has a thread diameter (Dp) corresponding to thread diameter of the lower jackscrew (5), the plunger rod (8) being in threaded communication with the lower jackscrew (5), a threaded mainly cylindrical spindle (10) having a thread diameter (Ds) corresponding to thread diameter of the upper jackscrew (6), the spindle (10) being in threaded communication with the upper jackscrew (6), a button (12) engageable with the spindle (10), by one thereof having a recess and the other having a protrusion matching said recess along a direction parallel to the primary axis of the spindle (10), a resilient means (17) normally keeping the button (12) in a disengaged position from the spindle (10), wherein said recess and protrusion are kept away from each other by the resilient means (17), and the engaged position is available by pushing and moving the button (12) against the force of the resilient means (17), and the thread diameter (Ds) of the spindle (10) being greater than the thread diameter (Dp) of the plunger rod (8).

BRIEF DESCRIPTION OF THE FIGURES

The figures, whose brief explanation is herewith provided, is solely intended for providing a better understanding of the present invention and is as such not intended to limit the scope of protection or the context in which said scope is to be interpreted in the absence of the description.

DETAILED DESCRIPTION OF THE INVENTION

Referring now the figures outlined above, the present invention proposes a drug delivery device (18) for liquid pharmaceuticals. In other words, the present invention proposes a drive mechanism for multi-dose injectors and a relevant device for multi-dose drug delivery. The device (18) is suitable for use as a medication delivery pen, in particular as a multi-dose insulin delivery pen for use by diabetic patients.

The liquid pharmaceuticals delivery device (18) comprises:

A mainly cylindrical main body (1), a cartridge (3) having a mainly cylindrical inner cavity with a volumetric capacity for accommodating multiple doses of a liquid pharmaceutical, the cartridge (3) comprising a first end for receiving a plunger (7) and a second end for liquid pharmaceutical extraction; the plunger (7) having a circumferential portion shaped and sized to correspond to the transversal section of the cartridge (3).

The device (18) further comprises:

A jackscrew (55) comprising a threaded lower jackscrew (5) and a threaded upper jackscrew (6) integrated or fixed to each other, the jackscrew (55) being rotatable around a primary axis (16) of the main body (1) and stationary along said primary axis (16), A threaded plunger rod (8) which is integrated to the plunger (7) and which has a thread diameter (Dp) corresponding to thread diameter of the lower jackscrew (5), the plunger rod (8) being in threaded communication with the lower jackscrew (5) and moving inside the lower bearing (4), wherein the lower bearing (4) together with plunger rod (8), and upper/lower jackscrews (5, 6) stays in permanent contact with the cartridge during dose setting and delivery in order to guarantee the dosing accuracy.

A threaded mainly cylindrical spindle (10) having a thread diameter (Ds) corresponding to thread diameter of the upper jackscrew (6), the spindle (10) being in threaded communication with the upper jackscrew (6).

A button (12) engageable with the spindle (10), by one thereof having a recess and the other having a protrusion matching said recess along a direction parallel to the primary axis of the spindle (10), A resilient means (17) normally keeping the button (12) in a disengaged position from the spindle (10), wherein said recess and protrusion are kept away from each other by the resilient means (17), and the engaged position is available by pushing and moving the button (12) against the force of the resilient means (17).

By means of the above mentioned features, further pushing the button (12) and linearly moving it along with the spindle (10) relative to the main body (1) towards the second end of the cartridge (3), enforces rotational movement of the lower jackscrew (5), translationally imposing the plunger rod (8) through the lower bearing (4) thus translationally moving the plunger (7) towards the second end of the cartridge (3) along the primary axis (16) of the main body (1). At this point, the force transmission to the cartridge (3) and plunger rod (8) is supported by the flange (20) of lower jackscrew (5) and the lower bearing (4), independent from the main body (1).

In operation:
- a dosage setting is made by partly unscrewing the number sleeve (9) from the main body (1),
- and a pharmaceuticals delivery is performed by pushing the button (12) towards the second end along a direction parallel to a primary axis (16) of the main body (1) thereby moving the plunger (7) towards the second end.

Figure 1:
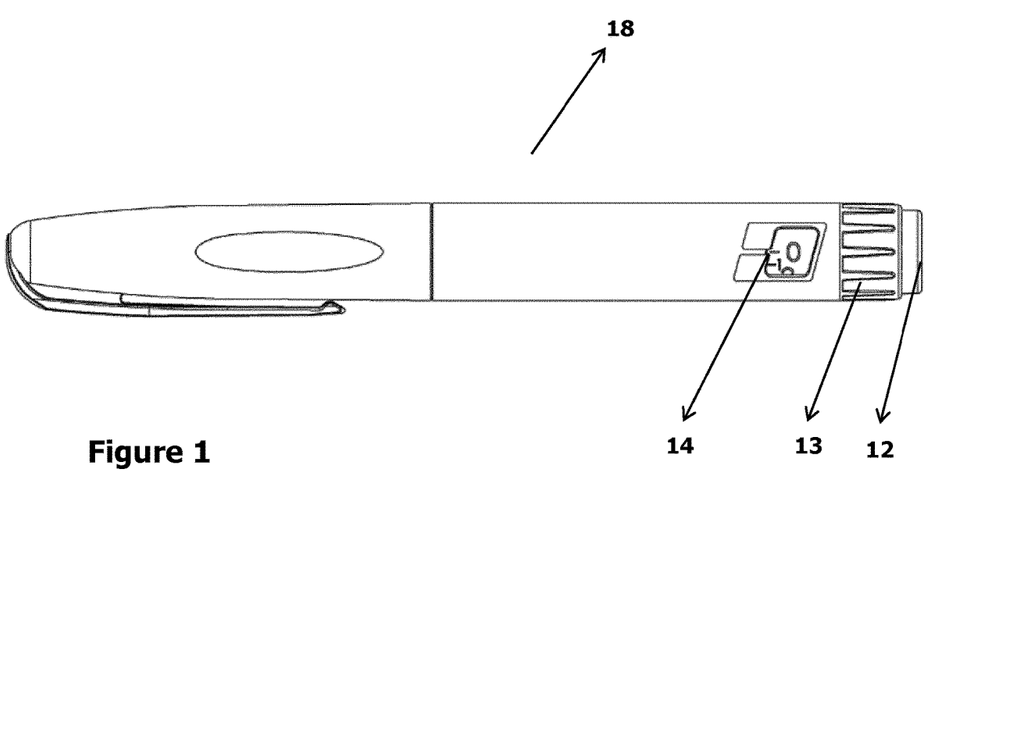
FIG. 1 shows exemplary side view of a device (18) according to the present invention with a cap for covering an injector needle for drug extraction therethrough.
Figure 2:
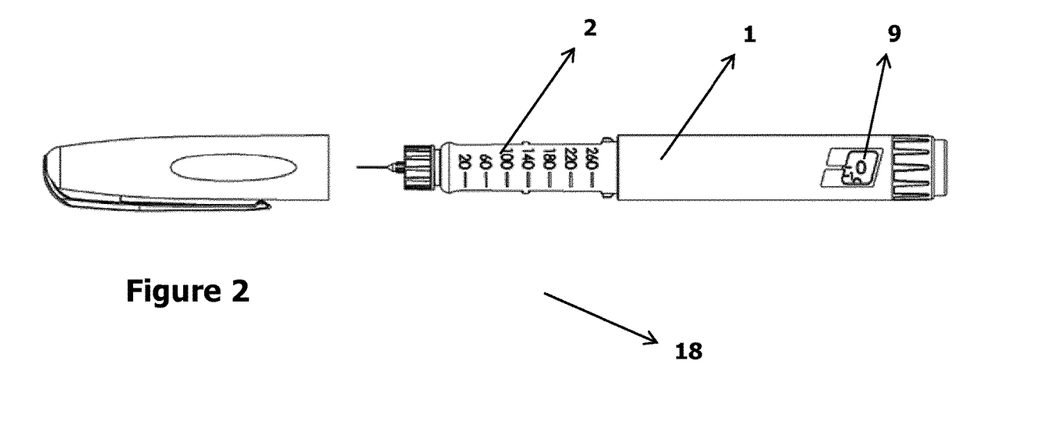
FIG. 2 shows exemplary side view of a device (18) according to the present invention wherein the cap is off and the needle is exposed.
Figure 3:
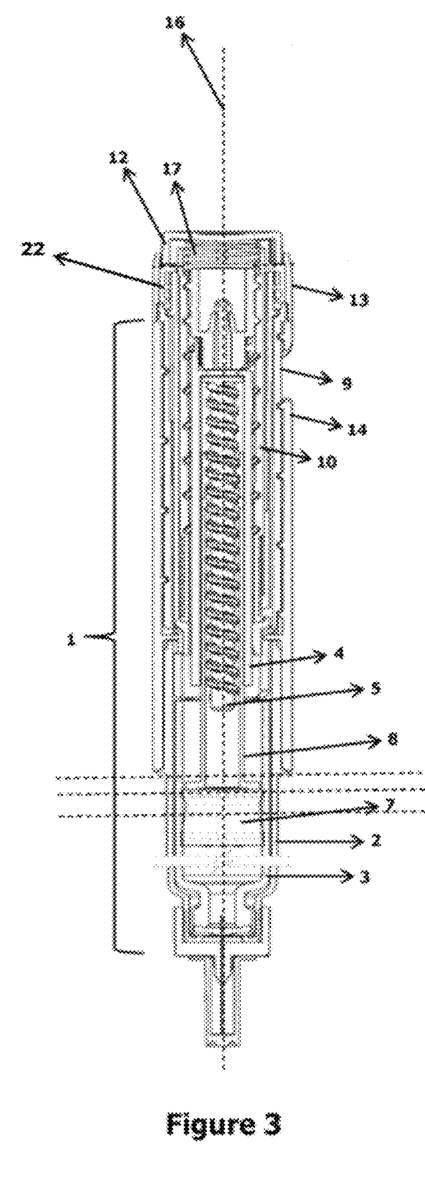
FIG. 3 shows exemplary longitudinal section of a device (18) according to the present invention upon drug delivery
Figure 4:
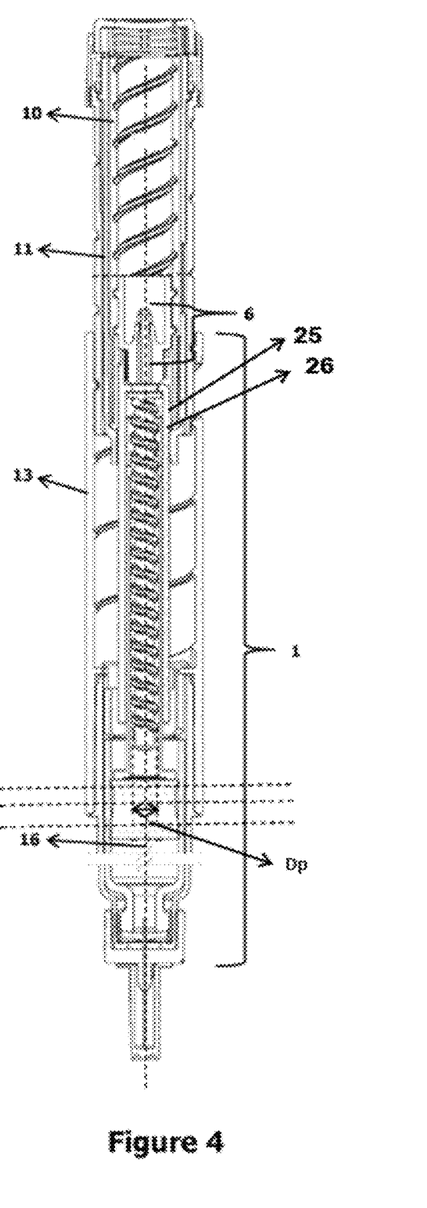
FIG. 4 shows exemplary longitudinal section of a device (18) according to the present invention at an armed state before drug delivery.
Figures 5, 6, 7:
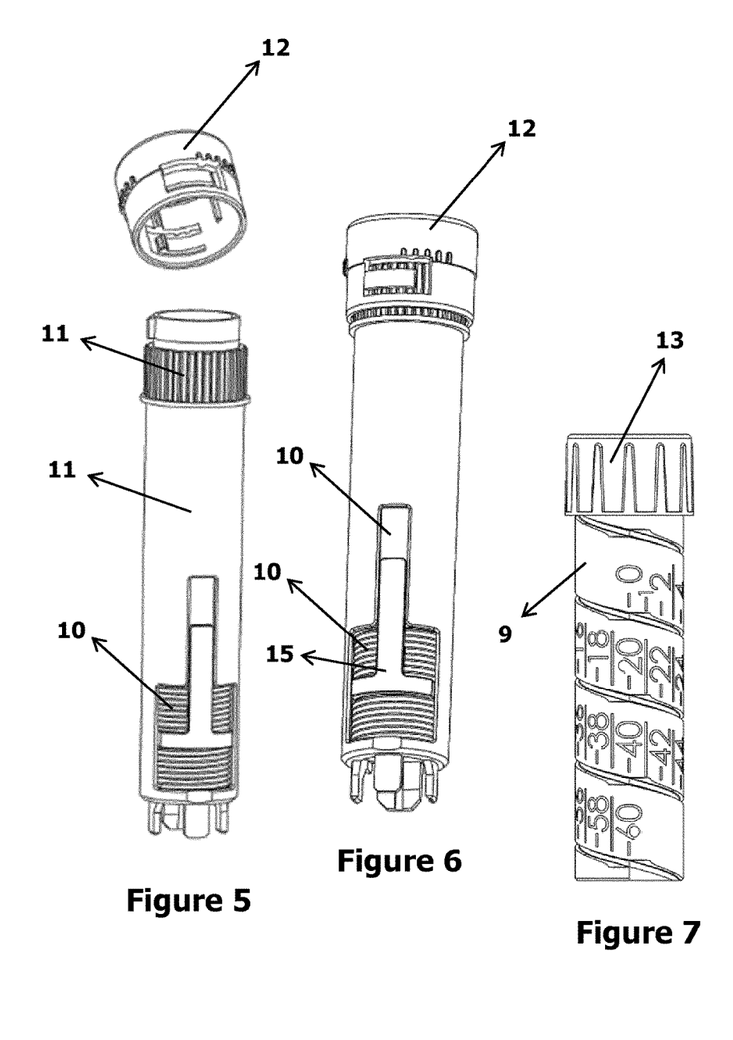
FIG. 5 partly exemplifies an assembling state of a device (18) according to the present invention that shows montage of the button (12) onto an assembly of spindle (10).
FIG. 6 partly exemplifies an assembling state of a device (18) according to the present invention that shows montage of the intermediate sleeve (11) and traveler (15).
FIG. 7 partly exemplifies an assembling state of a device (18) according to the present invention that shows montage of a number sleeve (9) with a dial grip (13), into a main body (1).
Figure 8:
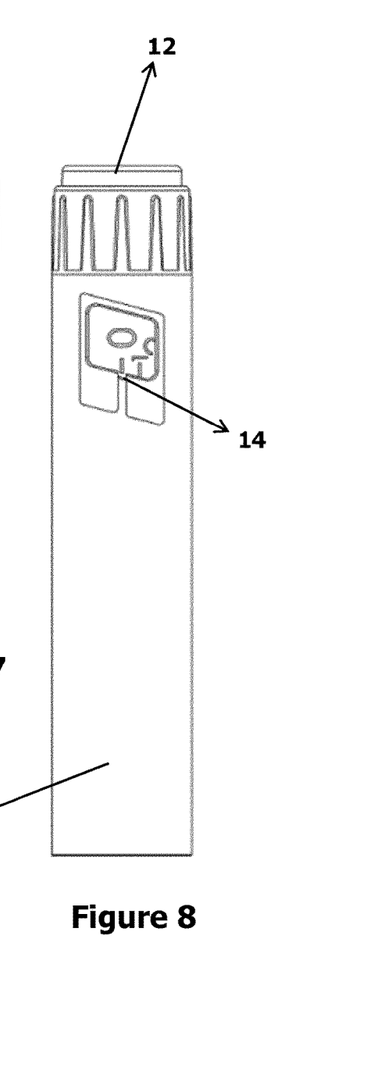
FIG. 8 partly exemplifies an assembling state of a device (18) according to the present invention that exemplifies mounted state of the features given in FIGS. 6 and 7.
Figure 9:
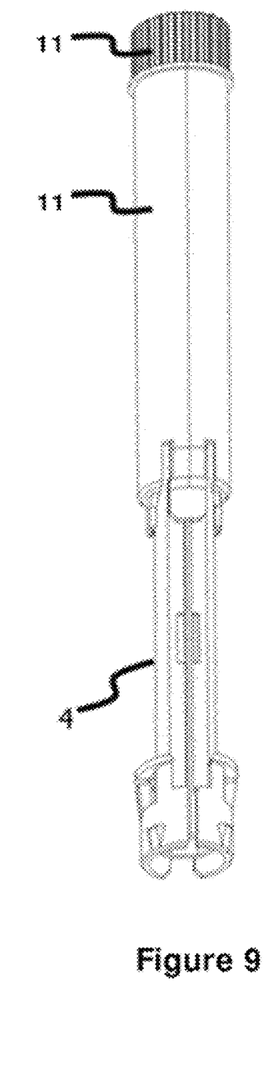
FIG. 9 represents an assembly of the lower bearing (4) and spindle (10).
Figures 10, 11, 12:
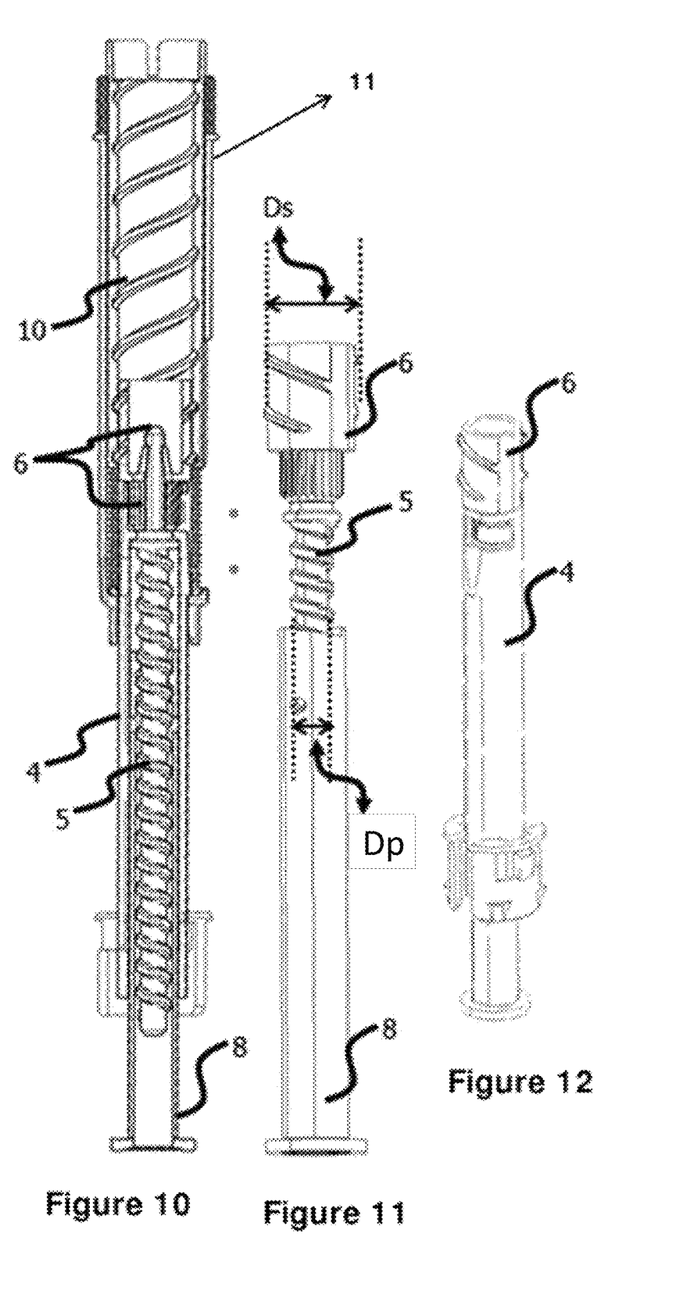
FIG. 10 represents an assembly of the lower bearing (4) and spindle (10) in FIG. 9 with the lower jackscrew (5), upper jackscrew (6) and plunger rod (8).
FIG. 11 represents an assembly of the lower (5) and upper jackscrews (6) with plunger rod (8). and lower bearing (4) with lower jackscrew (5) (and upper jackscrew (6), not shown)
FIG. 12 represents an assembly of the lower bearing (4) and the upper jackscrew (6).
Figures 13, 14:
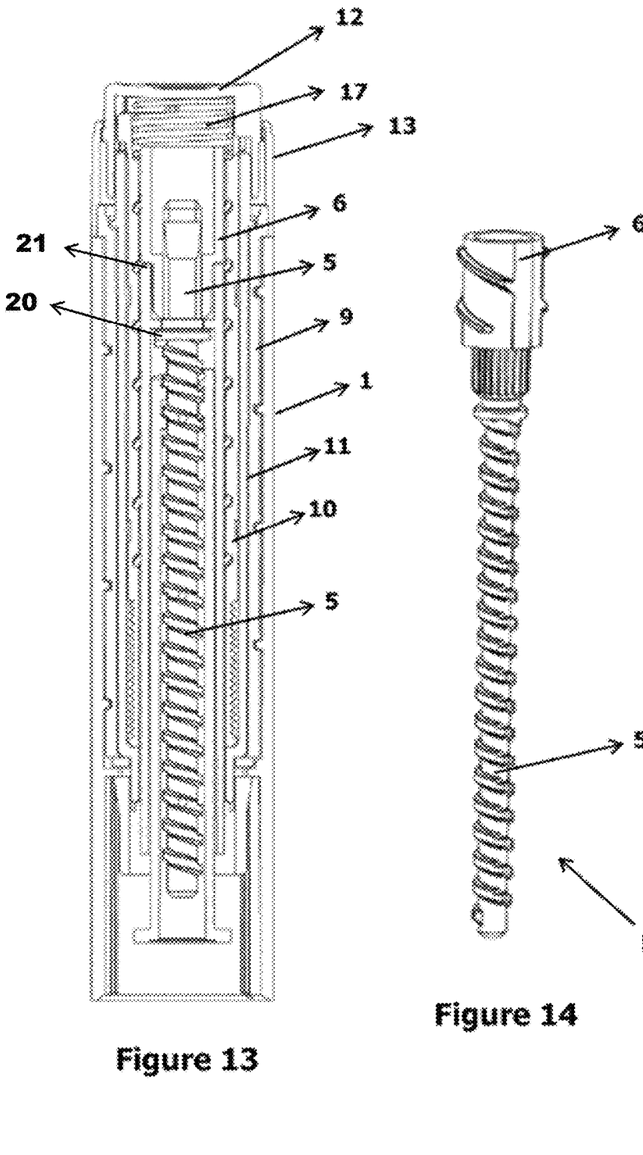
FIG. 13 detailedly exemplifies a portion of the device (18) according to the present invention more particularly an assembled main body (1) without cartridge (3) and cartridge holder (2).
FIG. 14 detailedly exemplifies an assembly of lower (5) and upper jackscrews (6).
Figure 15:
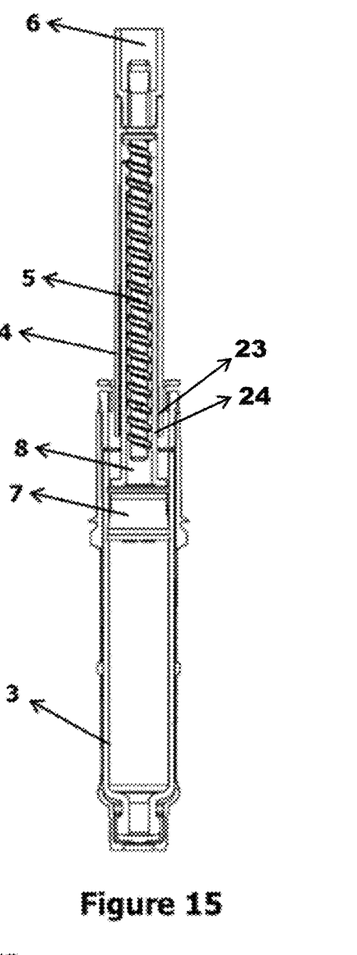
FIG. 15 detailedly represents mechanical assembly relationship between upper jackscrew (6), lower jackscrew (5), lower bearing (4), plunger rod (8), plunger (7) and cartridge (3) in a device (18) according to the present invention.
Figure 16:
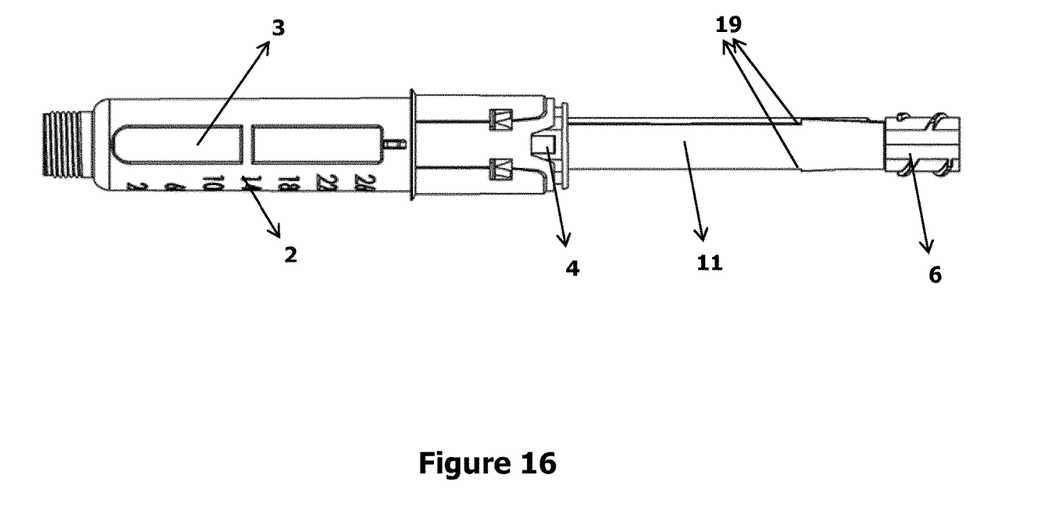
FIG. 16 shows the assembly of a permanent contact between the lower bearing (4) plunger rod (8), upper (6) and lower jacksrews (5) (lower jackscrew (5) is inside the plunger rod (8)) together with the cartridge (3) and cartridge holder (2) during dose setting and delivery.

The thread diameter (Ds) of the spindle (10) is greater than the thread diameter (Dp) of the plunger rod (8), as shown in FIG. 4. Thus, in operation, the torque at a thread of the plunger rod (8) is greater than the torque at a thread of the spindle (10). Thanks to the difference between thread diameters of plunger rod (8) and spindle (10), which are being herein named as Dp and Ds, respectively, force transmission is facilitated at drug delivery.

The facilitated force transmission here means that the force required to be applied onto the spindle (10) by pressing the button (12) is lower than the force required for moving the plunger (7) inside the cartridge (3). The former can be estimated by multiplying the latter by a Dp/Ds ratio, which is in this case lower than 1. The invention provides an easy to use drug delivery device by requiring relatively less force during subcutaneous self-administration of a liquid medicament.

In a preferred embodiment according to the present invention, the threads on the spindle (10) and the threads on the plunger rod (8) are working in the same rotational direction in order to reduce the operational friction. In addition, the threads on the spindle (10) have a pitch distance greater than a pitch distance of the threads on the plunger rod (8). Thus, in operation, the linear distance along a primary axis (16) covered by the spindle (10) is greater than that covered by the plunger rod (8). Thereby, whilst a delivery, linear motion range along the primary axis (16) is largest for the intermediate sleeve (11), and smallest for the plunger (7).

The device (18) according to the present invention preferably comprises the features in the following list:

A mainly tubular number sleeve (9) rotatably extendable out of the main body (1) and retractable there into, engaged with the main body (1) in a screw-socket relation, such that the number sleeve (9) is at least partly extended from the main body (1) at an armed position, and received by the main body (1) at a delivery position; said number sleeve (9) at least partly surrounding the spindle (10).

A mainly cylindrical intermediate sleeve (11) in-between the number sleeve (9) and the spindle (10), said intermediate sleeve (11) being rotatably connected to the number sleeve (9), and said intermediate sleeve (11) being at least partly surrounded by the number sleeve (9). The sleeve (11) also prevents the dosing mechanisms and lower bearing (4) to disconnect from the main body (1) and the lower bearing (4) has a fix stop edge (21) that corresponds to the stop edge (19) of the sleeve (11) to stop it from sliding. Also the thread end in the spindle (10) is blocked by the upper jack screw (6) from further rotation; this stops the sleeve (11) from sliding.

Preferably, the upper jackscrew (6) is ratchet on a longitudinal portion of a side surface thereof. In such embodiment, the device (18) further comprises a mainly tubular lower bearing (4) for linearly guiding the spindle (10) whilst an injection by at being least partly surrounded by the spindle (10). The lower bearing (4) is fixedly connected into the main body (1) and the cartridge hoder (2) is only fixed to the lower bearing (4), providing an independent block for the linear movement of the upper jackscrew (6) along a longitudinal axis (16) of the main body (1). The lower bearing (4) is preferably configured to selectively engage with the ratchet portion of the upper jackscrew (6), such that the lower bearing (4) blocks rotation of the upper jackscrew (6) in a first direction in accordance with extension of the number sleeve (9) out of the main body (1), and allows rotation of the jackscrew in a second direction opposite to the first direction in accordance with retraction of the number sleeve (9) into the main body (1).

Preferably, for further securing that the plunger (7) is effectively translated whilst an injection without rotation, the plunger rod (8) is longitudinally guided through the lower bearing (4) in vicinity of the first end of the cartridge (3), by means of:
- A (preferably longitudinal) recess on the plunger rod (8) and a corresponding protrusion on the lower bearing (4), or alternatively,
- A (preferably longitudinal) protrusion on the plunger rod (8) and a corresponding recess on the lower bearing (4). In other words, such preferred embodiment has the following features: the lower bearing (4) is provided with a lower bearing protrusion (23) and the plunger rod (8) is provided with a corresponding plunger rod recess (24), which recess being preferably longitudinal; or alternatively, the lower bearing (4) is provided with a recess and the plunger rod (8) is provided with a corresponding protrusion, which protrusion being preferably longitudinal Preferably, the lower bearing (4) has a longitudinal portion surrounding the lower jackscrew (5), and more preferably for further securing that the intermediate sleeve (11) is effectively translated along the primary axis (16) without rotating, the intermediate sleeve (11) is longitudinally guided along said longitudinal portion of the lower bearing (4), by means of:
- An intermediate sleeve recess (25) provided on the intermediate sleeve (11) and a corresponding longitudinal lower bearing protrusion (26) provided on the longitudinal portion of the lower bearing (4), or alternatively,
- A protrusion provided on the intermediate sleeve (11) and a corresponding longitudinal recess provided on the longitudinal portion of the lower bearing (4).

Preferably, the device comprises a cartridge holder (2) fixed to the lower bearing (4), for receiving a liquid pharmaceutical product cartridge (3). The cartridge holder (2) is preferably mainly tubular, for securing the cartridge (3) to the main body (1) with a higher stability.

Preferably an outer surface of the number sleeve (9) is provided with consecutive numbers relevant with dosage sizes.

Preferably, the main body (1) is provided with a pointer (14) for indicating a pharmaceutical volumetric dosage on the number sleeve (9), e.g. by aligning a dosage-related sign or number on the number sleeve (9) with the pointer (14).

The intermediate sleeve (11) preferably comprises an opening for receiving a threaded traveler (15). Said opening is configured to block any circumferential movement of the traveler (15) by having a circumferential width corresponding to a width of the traveler (15). The opening is further configured to limit longitudinal movement of the traveler (15) in a longitudinal direction parallel to a longitudinal primary axis (16). The spindle (10) has threads on a portion of its outer surface correspond with the threads of the traveler (15), such that when the spindle (10) is rotated, the traveler (15) moves thereon in a longitudinal direction parallel to the primary axis (16). The limited longitudinal movement of the traveler (15) along the primary axis (16) enables an irreversible migration of the traveler (15) towards a limit preferably indicating that there is no remaining liquid pharmaceutical in the cartridge (3) for a further dose to be delivered, or possibly indicating that there is no more liquid pharmaceutical in the cartridge (3).

Screw pitch at the spindle (10) threads corresponding to threads of the traveler (15) is preferably smaller than that at the threads of the plunger rod (8). This enables a precise migration of the traveler (15) along its limited motion range, throughout consumption of the pharmaceutical product.

Preferably, a portion of the number sleeve (9) is fixed to a dial grip (13). Thereby, arming of the device can be arranged by manually setting the number sleeve (9) by rotating the dial grip (13) around the primary axis (16).

In a preferred embodiment, the intermediate sleeve (11) has a circumferential ratchet portion (22) radially aligned with the dial grip (13); and the dial grip (13) has a protrusion in ratchet relation with said ratchet portion of the intermediate sleeve (11). Thereby an audible and/or haptic mechanical feedback is produced at rotating the dial grip (13) around the intermediate sleeve (11) at arming of the device.

Preferably, the upper jackscrew (6) has a circumferential ratchet portion on a side surface thereof, and the lower bearing (4) has a protrusion in communication with said ratchet portion of the upper jackscrew (6). Thereby, an audible and/or haptic mechanical feedback is produced at rotating the lower bearing (4) around the upper jackscrew (6) at a drug delivery by the device.

The present invention can be considered as further proposing an arming (i.e. dosage setting) method with a drug delivery device for preparation of the device for delivering a liquid pharmaceutical product, comprising:
- Unscrewing a mainly tubular number sleeve (9) from a mainly tubular main body (1), whereby the number sleeve (9) gets increasingly extracted from the main body (1) until a pointer (14) on the main body (1) aligns with a number on the number sleeve (9) indicating a volumetric dosage to be delivered, whereby the following simultaneous actions take place:
    - A mainly tubular intermediate sleeve (11) rotatably connected to an inner portion of the number sleeve (9) for allowing the number sleeve (9) rotate around the primary axis (16) relative to the main body (1); translationally extends from the main body (1) along with the number sleeve (9); the intermediate sleeve (11) further having a threaded portion on an inner surface;
    - and accordingly, a mainly tubular spindle (10) having threads on an inner surface thereof, rotates inside the intermediate sleeve (11), whilst extending from the main body (1) along with the intermediate sleeve (11).

Preferably, a traveler (15) engaged with threads on a portion of an outer surface of the spindle (10), makes a linear motion mainly parallel to a primary axis (16); being blocked against circumferential motions thereof with respect to the main body (1), and having a limited motion range in direction of the linear motion.

Preferably, the position of the traveler (15) is maintained with respect to the spindle (10).

Preferably, the arming is arranged by manually setting the number sleeve (9) via a dial grip (13) fixed to a portion of the number sleeve (9).

Preferably, the dial grip (13) has a protrusion in communication with a ratchet portion on an outer surface of the intermediate sleeve (11), such that an audible and/or haptic mechanical feedback is produced at rotating the dial grip (13) around the intermediate sleeve (11) at arming the device.

Preferably, the lower bearing (4) has a protrusion in communication with a ratchet portion on an outer surface of the upper jackscrew (6), such that an audible and/or haptic mechanical feedback is produced at rotating the lower bearing (4) around the upper jackscrew (6) at a drug delivery by the device.

Preferably, linear motion ranges of several portions of the device at arming and drug delivery steps with respect to the primary axis (16), are arranged in this ascending order among each other: plunger rod (8), and number sleeve (9); thus translational motion range at a delivery is largest for the number sleeve (9), and smallest for the plunger (7).

The present invention further proposes a drug delivery method performed with a drug delivery device for liquid pharmaceutical products, which is armed according to the method described above, comprising engaging a button (12) normally kept disengaged from the intermediate sleeve (11) by e.g. a resilient means (17) such as spring, by acting force thereon in a direction mainly parallel or identical to the primary axis (16), such that in an engaged state, force applied onto the button (12) prevents the intermediate sleeve (11) from rotating in accordance with any rotational movement of the number sleeve (9). Then, the following simultaneous actions take place:

The number sleeve (9) gets at least partly screwed into the main body (1),

Accordingly the intermediate sleeve (11) having a threaded portion on an inner surface makes a translational movement parallel to the primary axis (16); and Accordingly, a mainly tubular spindle (10) having a threaded portion on an outer surface, and which is received by the intermediate sleeve (11), makes a helical motion around an upper jackscrew (6), A threaded mainly cylindrical upper jackscrew (6), preferably having threads on a side surface thereof engaged with the threads of the spindle (10) rotates according to the translational motion of the spindle (10), whilst maintaining its axial position with regard to a primary axis (16); and a longitudinal lower jackscrew (5) fixed thereto and having a threaded portion on a side surface, rotates accordingly along with the upper jackscrew (6), A mainly cylindrical (preferably mainly tubular) plunger rod (8) having threads on a portion of a surface thereof engaged with the threads of the lower jackscrew (5), moves linearly in a direction opposite to that of the number sleeve (9), with regard to the primary axis (16); and a plunger (7) fixed to the plunger rod (8) linearly moves along the primary axis (16) accordingly, said plunger (7) being located inside a mainly tubular cartridge (3) for receiving a liquid pharmaceutical product, the cartridge (3) being fixed to the main body (1);

wherein, the traveler (15) maintains its position with respect to the spindle (10).

The lower bearing (4), lower jackscrew (5), upper jackscrew (6), plunger (7), plunger rod (8), and spindle (10) can be considered to form a driving mechanism in the device according to the present invention. The driving mechanism is permanently interlockable with the cartridge holder (2), preferably in a snap-fit manner. This provides accurate force transmission and dosing independent from main housing.

Since the parts of the driving mechanism (starting from the spindle (10) to the plunger rod (8) fixed/integral with the plunger (7)) are generally in threaded communication with each other, axial force transmission from user to the plunger (7) is reliable and easy. The linear motion range of the plunger (7) being shorter than that of the spindle (10), and accordingly shorter than that of the intermediate sleeve (11) gives opportunity to deliver a small dosage of pharmaceutical product by a long ranging linear motion with minimum effort by the user (accordingly, a minimum amount of force is required to be exerted onto the button (12)).

The thread diameter (Ds) at the spindle (10) (corresponding to the thread diameter at the upper jackscrew (6)) being larger than the thread diameter (Dp) at the plunger rod (8) (corresponding to the thread diameter at the lower jackscrew (5)), provides a reduction effect, thus the required force to be exerted by user at drug delivery (injection) for enforcing a linear motion to the plunger inside the cartridge, is minimized.

In a preferred embodiment depicted in the Figures, the plunger rod (8) is mainly in form of a tube with a threaded portion on an inner surface thereof, to engage with a threaded side surface of a lower jackscrew (5) mainly having a form of a threaded bar, the plunger rod (8) at least partly surrounding the lower jackscrew (5). This embodiment provides low-cost production of the plunger rod (8) as well as easy assembly of the device.

In an alternative embodiment, the lower jackscrew (5) is mainly in form of a tube with a threaded portion on an inner surface thereof to engage with a threaded side surface of a plunger rod (8) mainly having a form of a threaded bar; the lower jackscrew (5) at least partly surrounding the plunger rod (8).

In a drug delivery device (18) according to the present invention, the driving mechanism and cartridge are directly and permanently connected with preferably a single snap-on connection so that an accurate connection can be advantageously maintained in between the driving mechanism and the cartridge. In this way, the driving mechanism is in a permanent and robust connection with cartridge at arming and drug delivery stages. Additionally, the connection between driving mechanism and main body is mechanically supported in a stabile manner. And finally, the invention provides an easy to use drug delivery device by requiring the user to apply relatively less force during subcutaneous self-administration of a liquid medicament, such as insulin.

The invention claimed is:

1. A liquid pharmaceuticals delivery device (18) comprising a cylindrical main body (1), a cartridge (3) having a mainly cylindrical inner cavity with a volumetric capacity for accommodating multiple doses of a liquid pharmaceutical, the cartridge (3) comprising a first end for receiving a plunger (7) and a second end for liquid pharmaceutical extraction, the plunger (7) having a circumferential portion shaped and sized to correspond to a transversal section of the cartridge (3), wherein the device is characterized by further comprising:

a jackscrew (55) comprising a threaded lower jackscrew (5) and a threaded upper jackscrew (6) integrated to each other, the jackscrew (55) being rotatable around a longitudinal primary axis (16) of the cylindrical main body (1) and stationary along said longitudinal primary axis (16), a threaded plunger rod (8) integrated to the plunger (7) and having a thread diameter (Dp), which is smaller than the thread diameter (Ds) of a spindle (10), corresponding to the thread diameter of the lower jackscrew (5), the plunger rod (8) being in threaded communication with the lower jackscrew (5) and moving inside a lower bearing (4), wherein said lower bearing (4), together with plunger rod (8) and lower/upper jackscrews (5, 6), stays in permanent contact with the cartridge during dose setting and delivery in order to guarantee dosing accuracy as the force transmission to the cartridge (3) and plunger rod (8) is supported by a flange (20) of lower jackscrew (5) and the lower bearing (4), independent from the main body (1), the spindle (10) having threads and a thread diameter (Ds), which is greater than the thread diameter (Dp) of the plunger rod (8), corresponding to the thread diameter of the upper jackscrew (6), the spindle (10) being in threaded communication with the upper jackscrew (6), wherein the threads on the spindle (10) and the threads on the plunger rod (8) are working in the same rotational direction in order to reduce the operational friction and the threads on the spindle (10) have a pitch distance greater than a pitch distance of the threads on the plunger rod (8), a button (12) engageable with the spindle (10), by one thereof having a recess and the other having a protrusion matching said recess along a direction parallel to the primary axis of the spindle (10), and a resilient means (17) normally keeping the button (12) in a disengaged position from the spindle (10), wherein said recess and protrusion are kept away from each other by the resilient means (17), and the engaged position is available by pushing and moving the button (12) against the force of the resilient means (17), wherein the upper jackscrew (6) is ratchet on a longitudinal portion of a side surface thereof and the mainly tubular lower bearing (4) is at least partly surrounded by the spindle (10), fixedly connected into the main body (1), wherein a cartridge holder (2) is only fixed to the lower bearing (4), providing an independent block for the linear movement of the upper jackscrew (6) along the longitudinal primary axis (16) of the main body (1), wherein the lower bearing (4) is configured to selectively engage with the ratchet portion of the upper jackscrew (6), such that the lower bearing (4) blocks rotation of the upper jackscrew (6) in a first direction in accordance with extension of a number sleeve (9) out of the main body (1), and allows rotation of the jackscrew in a second direction opposite to the first direction in accordance with retraction of the number sleeve (9) into the main body (1).

2. The device (18) according to claim 1, wherein an outer surface of the number sleeve (9) is provided with consecutive numbers relevant with dosage sizes.

3. The device (18) according to claim 2, wherein the main body (1) is provided with a pointer (14) for indicating a pharmaceutical volumetric dosage on the number sleeve (9).

4. The device (18) according to claim 3, wherein an intermediate sleeve (11), positioned between the number sleeve (9) and the spindle (10), comprises an opening for receiving a threaded traveler (15), said opening being configured to block any circumferential movement of the traveler (15) by having a circumferential width corresponding to a width of the traveler (15), the opening being further configured to limit longitudinal movement of the traveler (15) in a longitudinal direction parallel to the longitudinal primary axis (16), and wherein the spindle (10) has threads on a portion of its outer surface corresponding the threads of the traveler (15).

5. The device (18) according to claim 4, wherein the intermediate sleeve (11) has a circumferential ratchet portion (22) radially aligned with a dial grip (13), and the dial grip (13) has a protrusion in mechanical communication with said ratchet portion (22) of the intermediate sleeve (11).

6. The device (18) according to claim 4, wherein the lower bearing (4) has a longitudinal portion surrounding the lower jackscrew (5), the intermediate sleeve (11) is longitudinally guided along said longitudinal portion of the lower bearing (4) by an intermediate sleeve recess (25) provided on the intermediate sleeve (11) and a corresponding longitudinal lower bearing protrusion (26) provided on the longitudinal portion of the lower bearing (4); or alternatively, by a protrusion provided on the intermediate sleeve (11) and a corresponding longitudinal recess provided on the longitudinal portion of the lower bearing (4).

7. The device (18) according to claim 2, wherein a circumferential portion on the number sleeve (9) is fixed to a dial grip (13).

8. The device (18) according to claim 1, wherein a segment of the threads of the spindle (10) corresponding to threads of a traveler (15) has a pitch distance that is smaller than a pitch distance of the threads of the plunger rod (8).

9. The device (18) according to claim 1, wherein the plunger rod (8) is mainly in the form of a tube with a threaded portion on an inner surface thereof to engage with a threaded side surface of a lower jackscrew (5) mainly having a form of a threaded bar, the plunger rod (8) at least partly surrounding the lower jackscrew (5).

10. The device (18) according to claim 1, wherein the lower bearing (4) is provided with a lower bearing protrusion (23) and the plunger rod (8) is provided with a corresponding plunger rod recess (24), which recess being preferably longitudinal; or alternatively, the lower bearing (4) is provided with a recess and the plunger rod (8) is provided with a corresponding protrusion, which protrusion being preferably longitudinal.

* * * * *